United States Patent [19]

Pawloski et al.

[11] Patent Number: 4,530,357
[45] Date of Patent: Jul. 23, 1985

[54] FLUID ACTUATED ORTHOPEDIC TOOL

[76] Inventors: James A. Pawloski, 189 Durfee St.;
Graham Williams, 801 South St.,
both of Southbridge, Mass. 01550;
James A. Pawloski, Jr., 2 Summit St.,
Webster, Mass. 01570

[21] Appl. No.: 486,097

[22] Filed: Apr. 18, 1983

[51] Int. Cl.³ .............................................. A61B 17/32
[52] U.S. Cl. ..................................... 128/312; 604/208
[58] Field of Search .................. 128/303 R, 305, 312,
128/346; 604/208

[56] References Cited

U.S. PATENT DOCUMENTS

| 1,002,826 | 9/1911 | DeVilbiss | 128/312 |
| 3,712,386 | 1/1973 | Peters | 128/305 |
| 3,752,161 | 8/1973 | Bent | 128/312 |
| 3,842,839 | 10/1974 | Malis et al. | 128/312 |
| 3,884,238 | 5/1975 | O'Malley et al. | 128/305 |
| 4,433,687 | 2/1984 | Burke et al. | 128/305 |
| 4,461,305 | 7/1984 | Cibley | 128/305 |

FOREIGN PATENT DOCUMENTS 382369 11/1964 Switzerland ..................... 128/346

Primary Examiner—Stephen C. Pellegrino
Assistant Examiner—Gene B. Kartchner
Attorney, Agent, or Firm—Arthur T. Fattibene

[57] ABSTRACT

A fluid actuated orthopedic tool for cutting away degenerated or torn cartilage which includes a housing having a piston chamber in which a piston is reciprocally mounted and an associated head portion. The head portion includes an elongated tubular guide having a fixed cutter member connected thereto, and through which there extends a rotatable shaft having a movable cutter member connected thereto. The rotary shaft is driving connected by a pinion to a piston rack so that the displacement of the piston by fluid pressure and spring return effects the actuation of the movable cutter member to effect a cutting action. A lock is provided to lock the cutter members, and an internal adjustment is provided to adjust the stroke of the piston. Also, a valve means and associated actuator is provided to control the flow of actuating fluid to the piston chamber.

3 Claims, 12 Drawing Figures

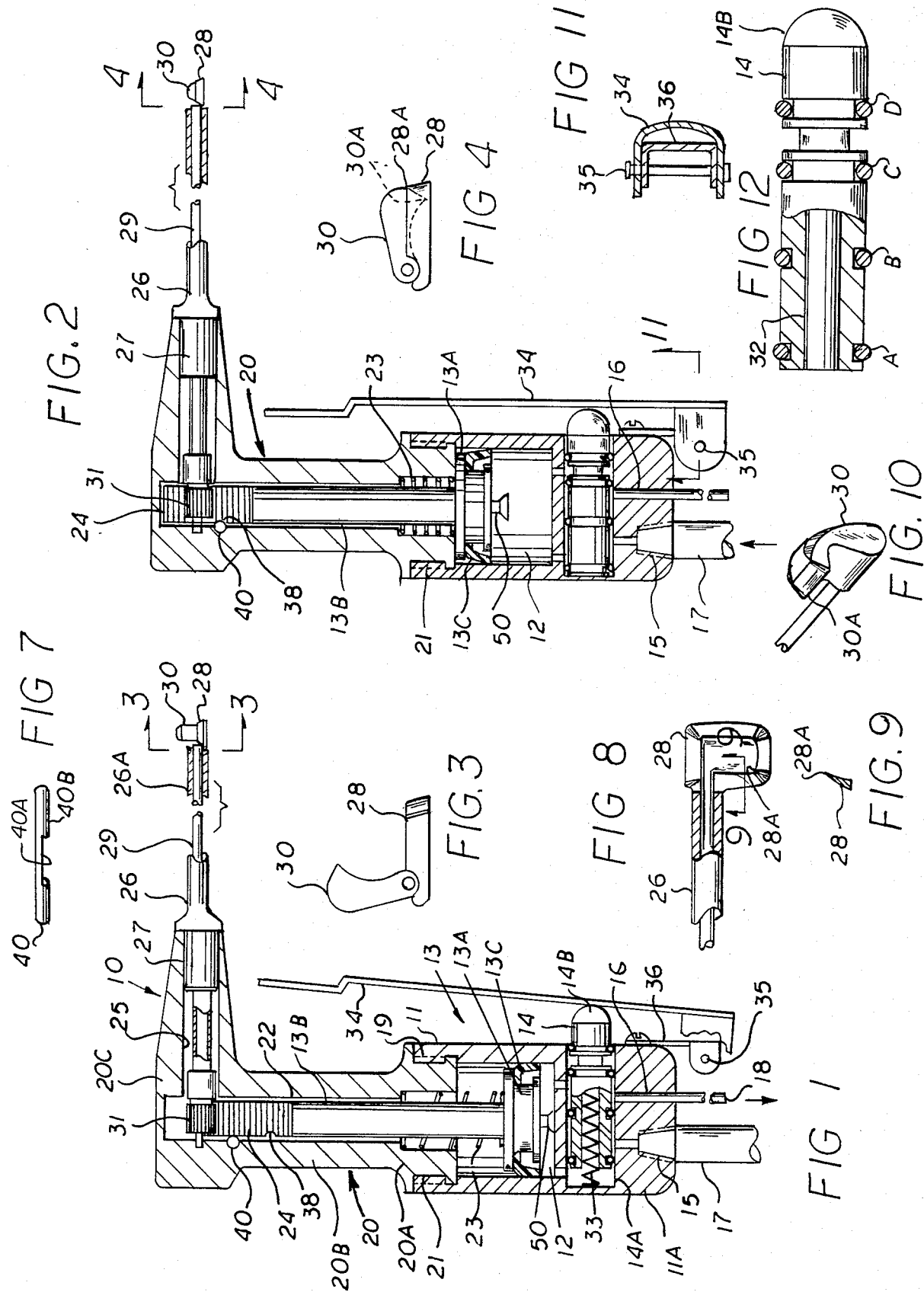

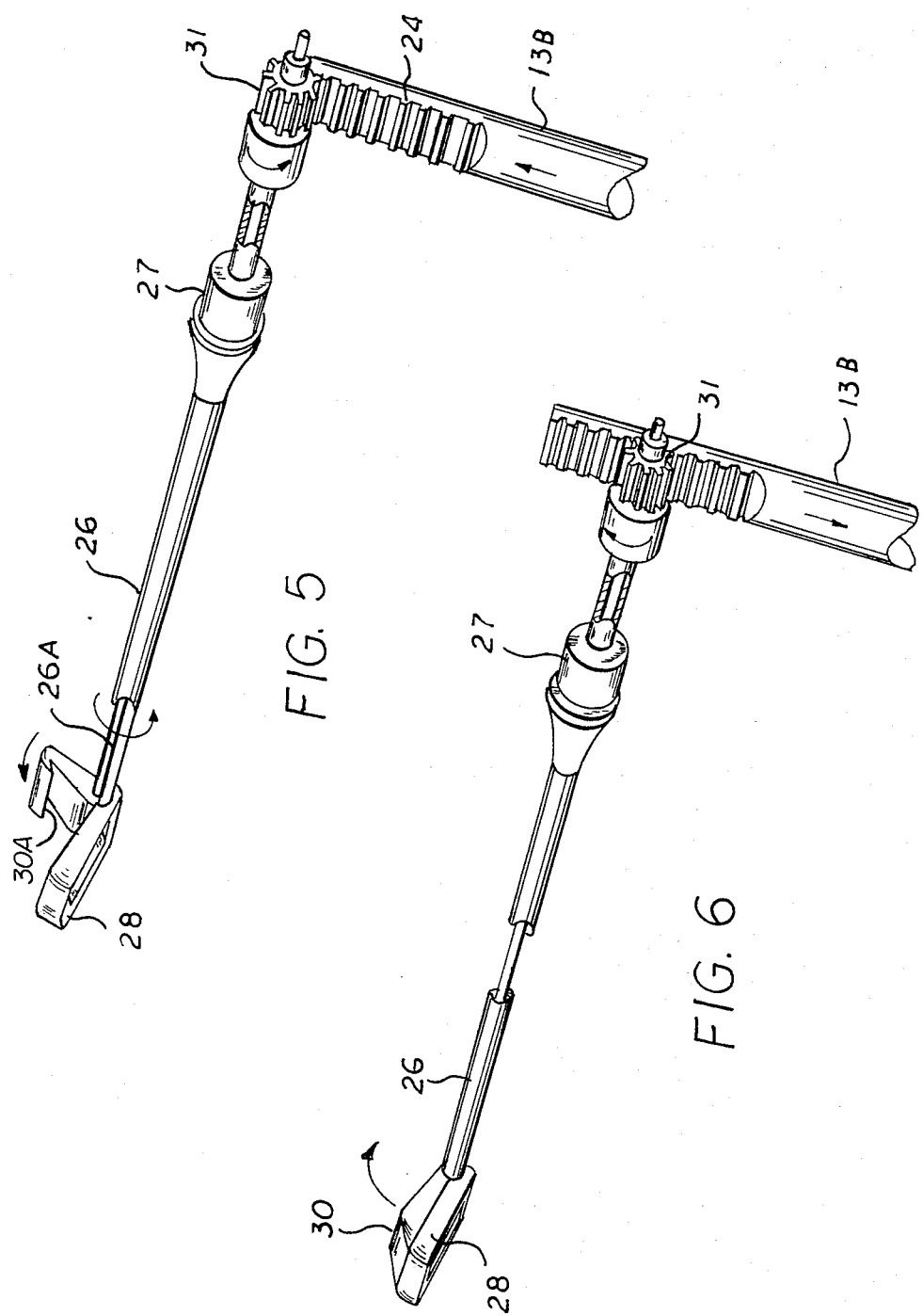

FLUID ACTUATED ORTHOPEDIC TOOL

PROBLEM AND PRIOR ART

Injuries to one's knee and other body joints which result in torn cartilages or damage thereto occur quite frequently, and is of particular concern to athletes and others. A surgical procedure which is presently gaining popular acceptance is one known as an orthoscopic meniscectomy. Such procedure requires the surgeon to make two small incisions about one quarter of an inch long adjacent the injury. Through one incision there is inserted an orthoscope which is a fiberoptic lighting and optical instrument whereby the surgeon can view the injured part. Through the other incision the surgeon inserts a surgical tool to snip and extract the injured tissue and/or bone chips. However, heretofore the surgical tools used in such procedures were manually actuated; and consisted of probes, grabbing instruments, scissors or a knife. While pneumatically actuated tools have been widely used in industry as wire cutters and other applications, e.g. as disclosed in U.S. Pat. No. 3,552,451, such tools are not suitable for surgical use.

OBJECTS

An object of this invention is to provide an improved pneumatically operated tool which is particularly applicable for use in orthoscopic surgery.

Another object is to provide an improved orthoscopic surgical tool that will expedite and enhance such surgery.

Another object is to provide an improved surgical tool which will minimize surgeon's fatigue and which is positive, efficient and safe in operation.

Another object is to provide an improved pneumatically operated surgical tool which can be readily autoclaved.

Another object is to provide a pneumatic surgical tool that will operate without lubrication.

Another object is to provide a pneumatic or fluid actuated surgical tool with a readily adjustable stroke.

SUMMARY OF THE INVENTION

The foregoing objects, features and advantages are attained by an improved surgical tool which comprises a housing to define a piston chamber in which a piston is reciprocally mounted. The end of the piston chamber is closed by a head which has projecting therefrom an elongated tubular guide which has a fixed cutter member connected to the extended end thereof. Extended through the tubular guide is a rotatable shaft to which the complementary movable cutter member or blade is attached which complements the fixed cutter member. The piston has connected thereto a piston rod having a rack portion disposed in meshing relationship to a pinion which is journal to the end of a cutter shaft whereby the reciprocation of the piston effects the actuation of the movable cutter or blade.

To actuate the piston, a valve assembly is provided to control the flow of a fluid pressure to and from the chamber to effect the displacement of the piston and the actuation of the cutter or blade accordingly. Also, the valve assembly includes a provision of exhausting the spent actuating fluid away from the site of the tool.

A lock is also provided whereby the cutter member can be maintained in a locked or inoperative position.

An adjustment is also provided to vary the stroke of the piston.

FEATURES

A feature of this invention resides in the provision of a surgical tool which is pneumatically actuated in accordance to the desire and/or need of the surgeon in the performance of a relatively delicate operation.

Another feature resides in the provision of a surgical cutting tool in which the reciprocation of a fluid actuated piston is transformed to an oscilating cutting motion of relatively movable complementary cutting members.

Another feature resides in the provision of a pneumatic surgical tool having a valve assembly arranged to discharge the exhausting fluid medium at a point remote from the site of the tool.

Another feature resides in the provision of a safety lock for the surgical tool.

Another feature resides in a built-in adjustment to vary the stroke of the piston and associated cutter accordingly.

Other features and advantages will become more readily apparent when considered in view of the drawings and detailed description in which:

FIG. 1 is a sectional view of the orthopedic tool embodying the invention with the parts shown in an inoperative position or non-cutting position.

FIG. 2 is a sectional view similar to that of FIG. 1 showing the parts in an operative or cutting position.

FIG. 3 is an enlarged detailed section view taken along line 3—3 on FIG. 1 to illustrate the cutter members in the inoperative position.

FIG. 4 is an enlarged detailed sectional view taken along line 4—4 on FIG. 2 showing the cutter members in the operative or cutting position.

FIG. 5 is an enlarged perspective view of the cutter assembly and drive shown in the inoperative position.

FIG. 6 is a view similar to that of FIG. 5 showing the cutter members in the operative position.

FIG. 7 is a detailed view of the lock pin.

FIG. 8 is a detailed plan view of the cutter member.

FIG. 9 is a sectional view taken along line 9—9 on FIG. 8.

FIG. 10 is a perspective view of the movable cutter.

FIG. 11 is a sectional view taken along line 11—11 on FIG. 2.

FIG. 12 is a detail view of the valve spool.

DETAILED DESCRIPTION

Referring to the drawings, there is shown a fluid actuated orthopedic tool 10 embodying the present invention. The tool 10 as will be herein described, is particularly developed to facilitate an orthoscopic surgical procedure; and which is especially applicable to remove damaged portions of tissue and/or cartilage from an injured joint.

As shown, the tool 10 comprises a main body or housing 11 which is defined as an opened end cylinder forming a piston chamber 12. The bottom of the housing is formed with a transversely extending bore 14A, which formes a valve chamber for accommodating a spool valve 14, as will be hereinafter described. Disposed in the bottom wall 11A of the housing 11 is a fluid inlet 15 and a fluid outlet 16. The fluid outlet is formed so that it can be readily coupled or connected to a flexible supply line 17, which directs the operating fluid medium, e.g. compressed air to the tool. The outlet 16 is connected to an exhaust line 18 which is sufficiently long so as to direct the exhausting fluid medium away from the operating area.

Connected to the upper or open end of the housing 11 is a head portion 20 for the tool. As shown, the open end of the housing 11 is provided with internal threads 19 which will complement the external threads 21 formed on the base 20A of the head portion 20. Extending upwardly from the base portion 20A is an elongated neck portion 20B to which there is connected a lateral extending mounting head 20C, to which the cutting means are attached as will be hereinafter described.

Reciprocally mounted within the chamber 12 is a piston assembly 13. The piston assembly 13 includes a piston head 13A having connected thereto a piston rod 13B which extends into a bore 22 that extends into the neck portion 20B. Circumscribing the piston head 13A is a cup type seal 13C to confine the operating fluid or medium between the piston head and the bottom of the piston chamber 12. A coil spring 23 is disposed about the piston rod 13B for maintaining a spring bias on the piston 13; and which spring 23, as will be hereinafter described, functions to return the piston when the air or fluid operating on the piston is exhausted through the outlet 16. The upper end of the piston rod 13B is provided with a rack 24.

The mounting head 20C is formed with a bore 25 which communicates with the bore 22 in the neck 20B and which extends laterally thereof. Connected to and projecting forward of the mounting head 20C is an elongated tubular guide 26. Mounted on the tubular guide 26 intermediate the ends thereof is a bushing 27 whereby the guide 26 is fitted to the end of the mounting head. The free end 26A of the guide is provided with a laterally disposed or fixed cutter member 28. As best seen in FIG. 8, the fixed cutter member 28 is generally U shaped with the ends of the U shaped cutter being connected to the guide 26, and it projects laterally therefrom.

Rotatable mounted within the tubular guide 26 is a shaft 29 which has connected to its extended end a movable cutter member or blade 30. As shown, the movable cutter blade 30 is shaped so as to closely complement the U shaped fixed cutter member 28 as best seen in FIG. 4. The arrangement is such that the complementary edges 28A and 30A of the respective cutter members 28 and 30, effect a shearing or cutting action on any tissue or material disposed therebetween when the movable cutter 30 is moved onto the fixed member 28.

Journalled to the other end of the rotary shaft 29 is a pinion 31, which is arranged to be in meshing relationship to the rack 24. The arrangement is such that the reciprocation of the rack 24 as the piston 13 is displaced, will transmit an oscilating movement to shaft 26 and the cutter 30 connected thereto, toward and away from the fixed cutter 28 to effect a scissor type cutting action.

To effect a controlled operation of the piston 13 and of the cutter members, a valve means is provided to control the flow of the activating medium into and out of the piston chamber 12. As shown, a spool valve 14 is disposed on the bore 14A to sequentially valve the inlet 15 and outlet 16 in a controlled manner to effect the displacement of the piston assembly by fluid pressure, e.g., compressed air.

As best seen in FIGS. 1 and 12, the spool valve 14 is provided within an internal bore 32 for receiving a spring 33 which functions to maintain the spool valve 14 is a position wherein it normally seals off the inlet 15 from the piston chamber 12, and where the piston chamber 12 is in open communication with the outlet 16 as best seen in FIG. 1. In the inoperative position, the head end 14B of the spool valve 14 projects outwardly of the valve bore or chamber 14A to bear against an actuator or operating lever 34 which is pivotally connected by a pivot pin 35 to a mounting bracket 36 secured to the body or housing 11.

As seen in FIGS. 1, 2 and 12 the spool valve 14 is provided with two sets of spaced apart sealing or "O" rings, i.e. "O" rings A,B and C,D. The respective "O" ring sets A,B and C,D as spaced on the spool valve 14 so that in the normal inoperative position of the spool valve 14, as shown in FIG. 1, the first set of "O" rings A,B are disposed to seal off the communication between the fluid inlet 15 and the piston chamber 12; while the second set of "O" rings, C,D, are positioned so as to place chamber 12 in communication with the exhaust or outlet 16. Thus, with fluid pressure sealed off from the piston chamber, the spring 23 acting on the piston head will normally maintain the piston in its inoperative, retracted position as seen in FIG. 1.

When the actuator or operating lever 34 is depressed as shown in FIG. 2, the spool valve 14 is displaced against the bias of its spring 33 so as to shift the spool valve so that the first set of "O" rings A,B are shifted to open the inlet 15 into communication with the piston chamber 12 while the second set of "O" rings, C,D, are displaced to seal off the chamber 12 from the outlet 16. Thus, the pressure of the fluid flowing in the piston chamber 12 effects the displacement of the piston head 13A and which in turn will cause the pinion 31 meshing with rack 24 to rotate the shaft 29 and cutter blade 30 connected thereto toward cutter member 28 to effect a cutting or snipping action. Upon release of the actuating handle or lever 34, the force of spring 33 of the spool valve 14, which was compressed, is released to shift the spool valve toward its inoperative position causing the spool valve to be shifted so that the inlet port 15 is sealed off from the piston chamber 12 and opening the exhaust or outlet port 16 so that the fluid pressure within the chamber 12 is vented, causing the spring 23 to return the piston to its inoperative position of FIG. 1. In so doing, the cutter member 30 is rotated to its inoperative position. By continued or repeated operation of the actuator 34, a surgeon can effect the cutting action of the cutter member in a controlled manner whereby the speed of the cutting action is controlled by the surgeon's actuation of the operating lever 34.

If desired, the tool 10 may be provided with a locking means to maintain the cutter members in their locked or closed position. This is attained by providing the piston rod with a notch, as noted at 38, which is adapted to coincide with a lock pin 40. The lock pin 40 comprises a pin having a flattened portion which is slidably mounted in a bore formed in the head to extend transversely thereof, and which is arranged to be displaced to either a locked or unlocked position. The lock pin 40 is provided with a flattened portion 40A, which in the unlocked position, is disposed so as to maintain the bore 22 unobstructed. To effect a locking of the cutter members in their closed or cutting position, the lock pin 40 is pushed into locking position when the locking notch 38 is brought into alignment with the lock pin. With the notch 38 disposed opposite the lock pin, and displacing the lock pin to its lock position, the rounded 40B portion of the pin 40 will engage the notch 38 and maintain the piston rod in a locked position.

A means may also be provided to adjust the stroke of the piston, which can be preset for any given tool. This is attained by providing an adjustment in the form of an adjusting screw 50 which may be threaded into the piston head to define an adjustable stop for the piston 13. Thus, by adjusting the length of the adjusting screw 50, the stroke of the piston can be adjusted accordly.

While the invention has been described with respect to a particular embodiment thereof, variations and modifications may be made without departing from the spirit or scope of the invention.

What is claimed is:

1. A fluid actuated orthorpedic tool comprising
a housing having a piston chamber formed therein, said chamber being open at one end,
a head means connected to said housing and defining an end closure at said one end,
a piston means slidably disposed within said piston chamber,
said piston means including a piston rod and a piston, said piston being connected to one end of said piston rod,
said piston rod having a pinion rack adjacent the other end of said piston rod,
a spring means acting on said piston for normally biasing said piston means toward an inoperative position,
said head means including a base, a connected elongated neck portion and a lateral extending mounting head portion,
said piston rod extending through the base and connected neck portion of said head means,
an elongated tubular guide connected to said lateral mounting head portion to define a lateral extension thereof,
cutter means including a fixed cutter member and a complimentary movable cutter member,
said fixed cutter member being connected to the projecting end of said tubular guide,
an elongated shaft rotatably journalled in said tubular guide,
and said movable cutter member being connected to said shaft for movement toward and away from said fixed cutter member as said shaft is rotated,
a pinion connected to said shaft wherein said pinion is disposed in meshing relationship with said rack to drive said shaft in one direction or the other as said piston is displaced within said piston chamber,
said housing having a fluid inlet and fluid outlet,
a valve means for controlling the flow of a fluid actuating medium to and from said piston chamber to actuate said piston and associated cutter means,
and a valve actuator connected to said valve means for actuating said valve means,
said valve means including a valve chamber disposed in said housing,
said valve chamber being in communication with said fluid inlet and fluid outlet and with said piston chamber,
a spool valve movably mounted in said valve chamber,
a spring means operating on said spool valve for normally biasing said spool valve toward its inoperative position and in engagement with said valve actuator,
and said spool valve including means for connecting said fluid inlet with said piston chamber and for sealing said piston chamber from said fluid outlet in the operative position of said spool valve and whereby said fluid inlet is sealed from said piston chamber and said piston chamber is connected to said fluid outlet in the inoperative position of said spool valve.

2. A fluid actuated orthopedic tool as defined in claim 1 and including locking means for locking said fixed and movable cutter members in their closed cutting position,
said locking means including a notch formed on said piston rod, and a complimentary lock pin, said lock pin being mounted adjacent said piston rod for lateral displacement relative to said piston rod, said locking pin having a flattened portion and protruding portion whereby said protruding portion is adapted to engage said notch in the locked position, and whereby said flattened portion is disposed opposite said piston rod in the unlocked position.

3. An orthopedic tool as defined in claim 1 and including means to adjust the stroke of said piston, said adjusting means including an adjusting screw threaded into said piston to define an adjustable stop for said piston.

* * * * *